(12) United States Patent
Painter et al.

(10) Patent No.: US 9,618,531 B2
(45) Date of Patent: Apr. 11, 2017

(54) OPTOMECHANICAL ACCELEROMETER

(71) Applicants: California Institute of Technology, Pasadena, CA (US); University of Rochester, Rochester, NY (US)

(72) Inventors: Oskar Painter, Sierra Madre, CA (US); Martin Winger, Meilen (CH); Qiang Lin, Rochester, NY (US); Alexander Krause, Alhambra, CA (US); Tim D. Blasius, Pasadena, CA (US)

(73) Assignees: CALIFORNIA INSTITUTE OF TECHNOLOGY, Pasadena, CA (US); UNIVERSITY OF ROCHESTER, Rochester, NY (US)

( * ) Notice: Subject to any disclaimer, the term of this patent is extended or adjusted under 35 U.S.C. 154(b) by 388 days.

(21) Appl. No.: 14/379,744

(22) PCT Filed: Mar. 1, 2013

(86) PCT No.: PCT/US2013/028763
§ 371 (c)(1),
(2) Date: Aug. 19, 2014

(87) PCT Pub. No.: WO2013/131067
PCT Pub. Date: Sep. 6, 2013

(65) Prior Publication Data
US 2015/0020590 A1    Jan. 22, 2015

Related U.S. Application Data

(60) Provisional application No. 61/606,272, filed on Mar. 2, 2012.

(51) Int. Cl.
*G01P 15/08* (2006.01)
*G01P 15/093* (2006.01)
(Continued)

(52) U.S. Cl.
CPC .......... *G01P 15/093* (2013.01); *B81B 3/0051* (2013.01); *B81B 3/0067* (2013.01);
(Continued)

(58) Field of Classification Search
CPC ......... G01P 3/36; G01P 15/093; B81B 3/0051
(Continued)

(56) References Cited

U.S. PATENT DOCUMENTS 6,613,601 B1    9/2003    Krauss et al.
7,355,720 B1    4/2008    Carr
(Continued)

FOREIGN PATENT DOCUMENTS

CN    200959015 Y    10/2007
CN    101782594    * 1/2010    ............ G01P 15/093

OTHER PUBLICATIONS

"Accelerometer Selection Based on Applications," accessed at https://web.archive.org/web/20150102114019/https://www.endevco.com/news/archivednews/2006/2006_08/2006_08_f4.pdf, accessed on Jan. 2, 2015, pp. 1-8.
(Continued)

*Primary Examiner* — Benjamin Schmitt
(74) *Attorney, Agent, or Firm* — Turk IP Law, LLC

(57) ABSTRACT

Technologies are generally described for operating and manufacturing optomechanical accelerometers. In some examples, an optomechanical accelerometer device is described that uses a cavity resonant displacement sensor based on a zipper photonic crystal nano-cavity to measure the displacement of an integrated test mass generated by acceleration applied to the chip. The cavity-resonant sensor may be fully integrated on-chip and exhibit an enhanced displacement resolution due to its strong optomechanical coupling. The accelerometer structure may be fabricated in a silicon nitride thin film and constitute a rectangular test
(Continued)

mass flexibly suspended on high aspect ratio inorganic nitride nano-tethers under high tensile stress. By increasing the mechanical Q-factors through adjustment of tether width and tether length, the noise-equivalent acceleration (NEA) may be reduced, while maintaining a large operation bandwidth. The mechanical Q-factor may be improved with thinner (e.g., <1 micron) and longer tethers (e.g., 10-560 microns).

24 Claims, 10 Drawing Sheets

(51) Int. Cl.
| | |
|---|---|
| B81B 3/00 | (2006.01) |
| B81C 1/00 | (2006.01) |
| B82Y 99/00 | (2011.01) |
| G01N 21/55 | (2014.01) |
| G01N 21/59 | (2006.01) |
| H01L 21/02 | (2006.01) |

(52) U.S. Cl.
CPC ........ *B81B 3/0083* (2013.01); *B81C 1/00015* (2013.01); *B82Y 99/00* (2013.01); *G01N 21/55* (2013.01); *G01N 21/59* (2013.01); *H01L 21/02373* (2013.01); *B81B 2201/0235* (2013.01); *G01N 2201/063* (2013.01); *G01N 2201/06113* (2013.01)

(58) Field of Classification Search
USPC ............................... 73/514.26; 356/496, 506
See application file for complete search history.

(56) References Cited

U.S. PATENT DOCUMENTS

| 8,849,075 | B2* | 9/2014 | Painter | G02B 26/001 |
| | | | | 385/129 |
| 2003/0206693 | A1 | 11/2003 | Tapalian et al. | |
| 2011/0103733 | A1 | 5/2011 | Tang et al. | |
| 2013/0119994 | A1* | 5/2013 | Csutak | G01V 3/30 |
| | | | | 324/338 |

OTHER PUBLICATIONS

"Model 752A12 / A13 ISOTRON® accelerometer," accessed at https://web.archive.org/web/20150102113402/https://www.endevco.com/datasheets/752A1.pdf, accessed on Jan. 2, 2015, pp. 1-3.
"Welcome to Lumedyne Technologies!," accessed at https:/web.archive.org/web/20130117041858/http://www.lumedynetechnologies.com/index.html, accessed on Jan. 2, 2015, p. 1.
Acar, C., and Shkel, A.M., "Experimental evaluation and comparative analysis of commercial variable-capacitance MEMS Accelerometers," Journal of Micromechanics and Microengineering, vol. 13, No. 5, pp. 634-645 (2003).
Allen, H.V., et al., "Accelerometer systems with self-testable features," Sensors and Actuators, vol. 20, No. 1-2, pp. 153-161 (Nov. 15, 1989).
Anetsberger, G., et al., "Measuring nanomechanical motion with an imprecision far below the standard quantum limit ," Physical Review A, vol. 82, pp. 061804-061804-5 (Dec. 29, 2010).
Berkoff, T.A., and Kersey, A.D., "Experimental demonstration of a fiber Bragg grating accelerometer," IEEE Photonics Technology Letters, vol. 8, No. 12, pp. 1677-1679 (Dec. 1996).
Camacho, R.M., et al., "Characterization of radiation pressure and thermal effects in a nanoscale optomechanical cavity," Optics Express, vol. 17, No. 18, pp. 15726-15735 (2009).
Corbitt, T., et al., "Optical Dilution and Feedback Cooling of a Gram-Scale Oscillator to 6.9 mK," Physical Review Letters, vol. 99, pp. 160801-160801-4 (Oct. 19, 2007).
Eichenfield, M., et al., "A picogram and nanometer scale photonic crystal opto-mechanical cavity," Nature, vol. 459, pp. 550-555 (May 28, 2009).
Genes, C., et al., "Ground-state cooling of a micromechanical oscillator: Comparing cold damping and cavity-assisted cooling schemes," Physical Review A, vol. 77, pp. 033804-033804-9 (2008).
Kippenberg, T.J., and Vahala, K.J., "Cavity Opto-Mechanics," Optics Express, vol. 15, No. 25, pp. 17172-17205 (2007).
Kleckner, D., and Bouwmeester, D., "Sub-kelvin optical cooling of a micromechanical resonator," Nature, vol. 444, pp. 75-78 (Nov. 2, 2006).
Krishnamoorthy, U., et al., "In-plane MEMS-based nano-g accelerometer with sub-wavelength optical resonant sensor," Sensors and Actuators A: Physical, vol. 145-146, pp. 283-290 (Jul.-Aug. 2008).
Krishnan, G., et al., "Micromachined High-Resolution Accelerometers ," Journal of the Indian Institute of Science, vol. 87, No. 3, pp. 333-361 (Jul.-Sep. 2007).
Kölah, H., et al., "Noise Analysis and Characterization of a Sigma-Delta Capacitive Microaccelerometer," IEEE Journal of Solid-State Circuits, vol. 41, No. 2, pp. 352-361 (Feb. 2006).
Li, Y.T., et al., "Air Damped Capacitance Accelerometers and Velocimeters," IEEE Transactions on Industrial Electronics and Control Instrumentation, vol. 17, No. 2, pp. 44-48 (Apr. 1970).
Lin, Q., et al., "Mechanical oscillation and cooling actuated by the optical gradient force," Phys. Rev. Lett., vol. 103, pp. 103601-103601-4, Published Aug. 31, 2009.
Liu, C-H., et al., "Characterization of a high-sensitivity micromachined tunneling accelerometer vvith micro-g resolution," Journal of Microelectromechanical Systems, vol. 7, No. 2, pp. 235-244 (Jun. 1998).
Michael, C.P., et al., "An optical fiber-taper probe for wafer-scale microphotonic device characterization," Optics Express, vol. 15, No. 8, pp. 4745-4752 (Apr. 16, 2007).
Nakstad, H., and Kringlebotn, J.T., "Oil and gas applications: probing oil fields," Nature Photonics, vol. 2, pp. 147-149 (Mar. 2008).
Noell, W., et al., "Applications of SOI-based optical MEMS," IEEE Journal on Selected Topics in Quantum Electronics, vol. 8, No. 1, pp. 148-154 (Jan.-Feb. 2002).
Stipe, B.C., et al., "Noncontact friction and force fluctuations between closely spaced bodies," Phys. Rev. Lett, vol. 87, No. 9, pp. 096801-096801-4, (Aug. 27, 2001).
Tadigadapa, S., and Mateti, K., "Piezoelectric MEMS sensors: state-of-the-art and perspectives," Measurement Science and Technology, vol. 20, No. 9, pp. 1-30 (2009).
Verbridge, S.S., et al., "High quality factor resonance at room temperature with nanostrings under high tensile stress," Journal of Applied Physics, vol. 99, No. 12, pp. 124304-124304-8 (Jun. 2006).
Yasumura, K.Y., et al., "Quality Factors in Micron- and Submicron-Thick Cantilevers," Journal of Systems, vol. 9, No. 1, pp. 117-125 (Mar. 2000).
Yazdi, N., et al., "Micromachined Inertial Sensors," Proceedings of the IEEE, vol. 86, No. 8, pp. 1640-1659 (Aug. 1998).
Zandi, K., et al., "In-plane silicon-on-insulator optical MEMS accelerometer using waveguide fabry-perot microcavity with silicon/air bragg mirrors," IEEE 23rd International Conference on Micro Electro Mechanicai Systems (MEMS), pp. 839-842 (Jan. 24-28, 2010).
Zwahlen, P., et al., "Navigation grade MEMS accelerometer," IEEE 23rd International Conference on Micro Eiectro Mechanical Systems (MEMS), pp. 631-634 (Jan. 24-28, 2010).
International Search Report and Written Opinion for PCT/US2013/028763 filed Mar. 1, 2013, mailed Apr. 3, 2013.
Krause et al., "A Microchip Optomechanical Accelerometer"; paper submitted to Cornell University Library, Mar. 2, 2012.
Krause et al., "A High-Resolution Microchip Optomechanical Accelerometer", Nature Photonics, Published Online: Oct. 2012.

(56) References Cited

OTHER PUBLICATIONS

Painter, et al. "Chip-Scale, Ultra-Sensitive Optomechanical Accelerometer/Force Sensors", Quantum Assisted Sensing and Readout (QuASAR), Sep. 27, 2010.
Winger, et al. "A Chip-Scale Integrated Cavity-Electro-Optomechanics Platform", vol. 19, No. 25 / OPTICS EXPRESS 24905, Dec. 5, 2011.
Chan, et al., "Optical and Mechanical Design of a "Zipper" Photonic Crystal Optomechanical Cavity", Optics Express, vol. 17, Iss. 5, pp. 3802-3817, Mar. 2, 2009.
Hutchison et al., "Z-Axis Optomechanical Accelerometer", OxideMEMS Laboratory, Cornell University, Ithaca NY, USA.; MEMS 2012, Jan. 29-Feb. 2, 2012.
Eichenfield, "Cavity Optomechanics in Photonic and Phononic Crystals: Engineering the Interaction of Light and Sound at the Nanoscale"; Dissertation (Ph.D.), California Institute of Technology; Feb. 5, 2010.
Mao, et al., A Theoretical Study of a Nano-Opto-Mechanical Sensor Using a Photonic Crystal-Cantilever Cavity; IOP Science; Journal of Optics; vol. 14, No. 7; Published Jul. 9, 2012.
Armani, et al. "Ultra-High-Q Toroid Microcavity on a Chip", Letters to Nature; vol. 421; Feb. 27, 2003.
Retrieved from "http://en.wikipedia.org/w/index.php?title=Cavity_opto-mechanics&oldid=521773977" Categories: Optics; Wikipedia, Nov. 7, 2012.
Sridaran, et al. "Electrostatic Actuation of Silicon Optomechanical Resonators", Optics Express 9026; vol. 19, No. 10, May 9, 2011.
Gong, et al. "Low Power Resonant Optical Excitation of an Optomechanical Cavity", Optics Express 1440, vol. 19, No. 2, Jan. 17, 2011.
Thourhout, et al. "Optomechanical Device Actuation Through the Optical Gradient Force", Nature Photonics, vol. 4, Apr. 2010.
Kippenberg, et al. "Cavity Opto-Mechanics", Cornell University Library; arXiv:0712.1618v1 {physics.optics}, Dec. 10, 2007.
Li, et al. "Design of Dispersive Optomechanical Coupling and Cooling in Ultrahigh-Q/V Slot-Type Photonic Crystal Cavities", Optic Express 23856, vol. 18, No. 23, Nov. 8, 2010.
Sun, et al. "A Superhigh-Frequency Optoelectromechanical System Based on a Slotted Photonic Crystal Cavity", Cornell University Library, http://arxiv.org/physics/;arxiv:1210.3081; Oct. 10, 2012.
"RF MEMS", Wikipedia, Retrieved from "http://en.wikipedia.org/w/index.php?title=RF_MEMS&oldid=522819262" Categories: Microelectronic and microelectromechanical systems. Nov. 13, 2012.
Kippenberg, "Cavity Optomechanics: Back-Action Cooling of Mechanical Oscillators", Abstract, retrieved Aug. 19, 2014.
International Preliminary Report on Patentability for PCT/US2013/028763 filed Mar. 1, 2013, mailed on Sep. 12, 2014, issued Sep. 2, 2014.

* cited by examiner

OPTOMECHANICAL ACCELEROMETER

CROSS-REFERENCE TO RELATED APPLICATIONS

This Application is the U.S. National Stage filing of PCT Application Serial No. PCT/US 2013/028763 filed on Mar. 1, 2013 and claims priority to the PCT Application under 35 U.S.C. §371. This Application also claims priority to U.S. Provisional Application Ser. No. 61/606,272 filed on Mar. 2, 2012. Disclosures of both applications are incorporated by reference herein.

BACKGROUND

Unless otherwise indicated herein, the materials described in this section are not prior art to the claims in this application and are not admitted to be prior art by inclusion in this section.

The monitoring of accelerations is essential for a variety of applications ranging from inertial navigation to consumer electronics. The basic operation principle of an accelerometer is to measure the displacement of a flexibly mounted test mass. Sensitive displacement measurement may be realized using capacitive, piezo-electric, tunnel-current, or optical techniques. While optical readout provides superior displacement resolution and resilience to electromagnetic interference, conventional optical accelerometers either do not allow for chip-scale integration or involve bulky test masses.

SUMMARY

The present disclosure generally describes techniques for manufacturing and operating an optomechanical accelerometer.

According to some examples, an optomechanical accelerometer device may be provided. An optomechanical accelerometer device may include a frame, a test mass, a plurality of nano-tethers coupling the test mass to the frame, and a zipper cavity structure formed by a portion of the test mass and an adjacent portion of the frame.

According to other examples, an optical microelectromechanical system (OMEMS) device for detecting acceleration may be provided. An example OMEMS device may include an optomechanical accelerometer with a frame, a test mass, a plurality of nano-tethers coupling the test mass to the frame, and a zipper cavity structure formed by a portion of the test mass and an adjacent portion of the frame and electrostatic tuning capacitors. The OMEMS device may further include an optical beam source configured to direct a light beam onto the zipper cavity structure and an optical detector configured to detect a displacement of the test mass caused by an in-plane acceleration of the frame.

According to further examples, a method for operating an optomechanical accelerometer device may be provided. An example method may include one of transmitting a light beam through and reflecting a light beam from a zipper cavity structure of the accelerometer device, where the accelerometer device includes a frame, a test mass, a plurality of nano-tethers coupling the test mass to the frame, and the zipper cavity structure formed by a portion of the test mass and an adjacent portion of the frame. The method may further include detecting a displacement of the test mass caused by an in-plane acceleration of the frame by monitoring an effect of the zipper cavity structure on the transmitted light beam.

According to yet other examples, a method for fabricating an optomechanical accelerometer device may be provided. An example method may include forming a mask for accelerometer structures comprising a test mass, support nano-tethers, and a zipper cavity structure and transferring the mask into a silicon nitride layer formed on a single-crystal silicon wafer.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The foregoing and other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

DETAILED DESCRIPTION

Figure 1:
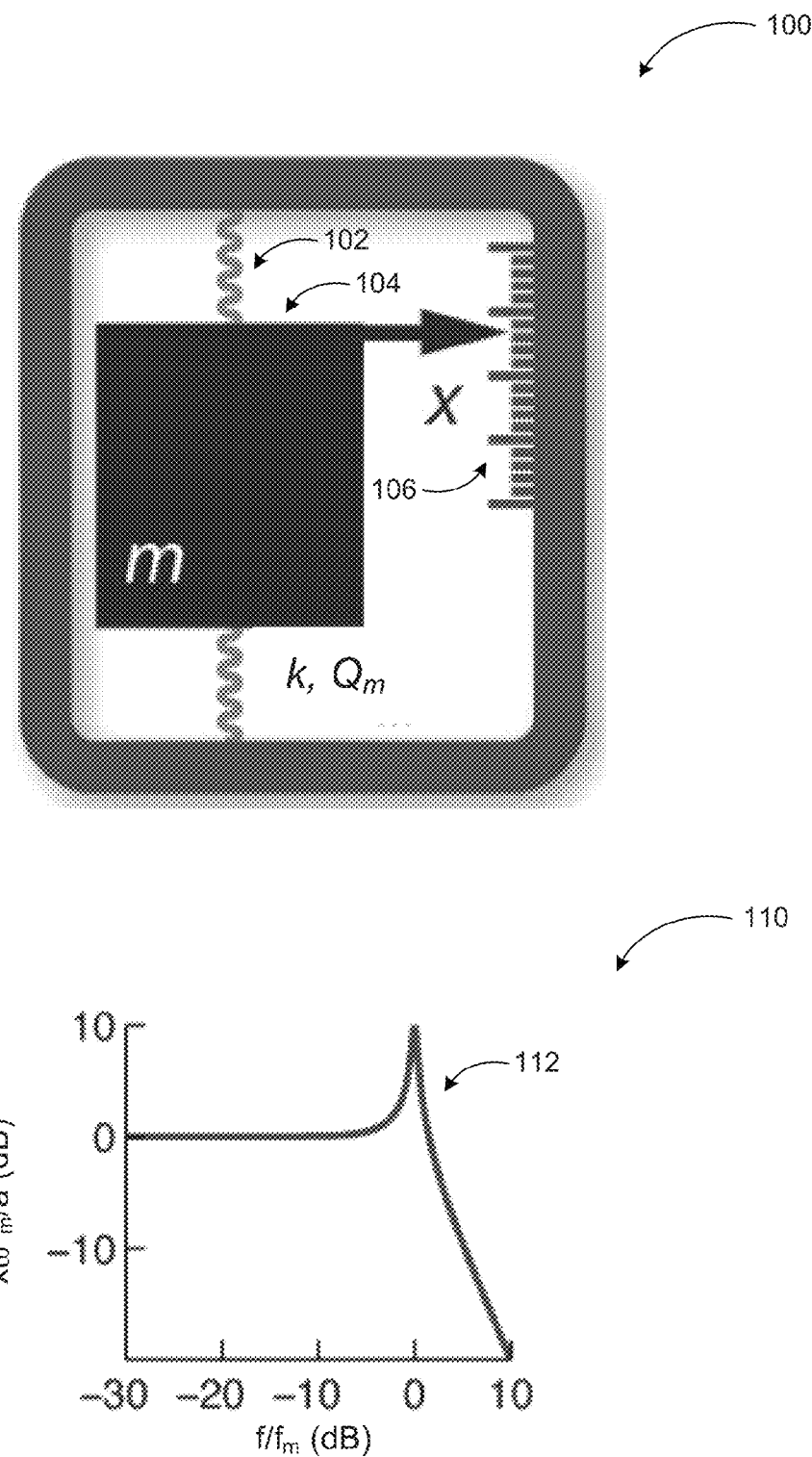
FIG. 1 illustrates an example accelerometer and the frequency response of the example accelerometer.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

This disclosure is generally drawn, inter alia, to methods, apparatus, systems, devices, and/or computer program products related to operating and manufacturing optomechanical accelerometers.

Briefly stated, technologies are generally described for operating and manufacturing optomechanical accelerometers. In some examples, an optomechanical accelerometer device is described that uses a cavity resonant displacement sensor based on a zipper photonic crystal nano-cavity to measure the displacement of an integrated test mass generated by acceleration applied to the chip. The cavity-resonant sensor may be fully integrated on-chip and exhibit an enhanced displacement resolution due to its strong optomechanical coupling. The accelerometer structure may be fabricated in a silicon nitride thin film and constitute a rectangular test mass flexibly suspended on high aspect ratio inorganic nitride nano-tethers under high tensile stress. By increasing the mechanical Q-factors through adjustment of tether width and tether length, the noise-equivalent acceleration (NEA) may be reduced, while maintaining a large operation bandwidth. The mechanical Q-factor may be improved with thinner (e.g., <1 micron) and longer tethers (e.g., 10-560 microns).

FIG. 1 illustrates an example accelerometer and the frequency response of the example accelerometer.

As shown in diagram 100, an accelerometer includes a test mass (m) 104, which when subjected to an acceleration $a(\omega)$ at frequency $\omega$(102) experiences a displacement $x(\omega) = \chi(\omega) \cdot a(\omega)$ proportional to the mechanical susceptibility $\chi^{-1}(\omega) = \omega^2_m - \omega^2 + i(\omega \cdot \omega_m)/Q_m$. Here $\omega_m$ is the angular resonance frequency of the oscillator and $Q_m$ is the mechanical quality factor. Put another way, when the accelerometer experiences a constant acceleration a, the test mass 104 may undergo a displacement of x (106)=ma/k. Diagram 110 illustrates the frequency response plot 112 of such an example accelerometer for $Q_m$=10 in a log-log format. As mentioned previously, accelerometers are typically operated below their fundamental resonance frequency $\omega_m$, where $\chi(\omega)=1/\omega^2_m$ exhibits an almost flat frequency-response as shown in the plot 112.

In a cavity optomechanical system, a mechanically compliant electromagnetic cavity may be used to resonantly-enhance read out of mechanical motion. Such systems may enable motion detection measurements with an imprecision at or below the standard quantum limit (SQL), corresponding to the position uncertainty in the quantum ground state of the mechanical object. The actual displacement sensitivity may reach the SQL for an ideal cavity system (no parasitic losses) due to fluctuating radiation pressure forces arising from shot noise of the probe light. The average radiation pressure force, on the other hand, may be relatively large in micro- and nano-scale optomechanical devices, and may offer a capability to control the sensor bandwidth via the optical spring effect and the sensor's effective temperature via passive damping or feedback cold-damping.

Due to the rapid development of silicon micro machining technology, microelectromechanical systems (MEMS) accelerometers have become exceedingly popular. Evolving from airbag deployment sensors in automobiles to tilt-sensors in cameras and consumer electronics products, MEMS accelerometers may be found in a large variety of technological applications with diverse needs of their performance metrics.

Inertial sensors are commonly used in navigation, guidance, balancing, human interface, and similar applications. Depending on a type of application (three dimensional, planar, or linear), one, two, or three accelerometers may be positioned with orthogonal measuring axes to measure inertial acceleration along respective axes.

While sensors for inertial navigation systems need low noise levels and superior bias stability, large bandwidths are needed for sensors in acoustics and vibrometry applications. However, there may be a fundamental tradeoff between noise performance and bandwidth. When subjected to an acceleration at a frequency, a mechanically compliant test mass will experience a displacement proportional to the mechanical susceptibility. Accelerometers may typically be operated below their fundamental resonance frequency leading to a tradeoff between resolution and bandwidth, since the large resonance frequency needed for high-speed operation may result in vanishingly small displacements. As a result, the performance of the displacement sensor may constitute a central figure of merit of an accelerometer.

Figure 2A:
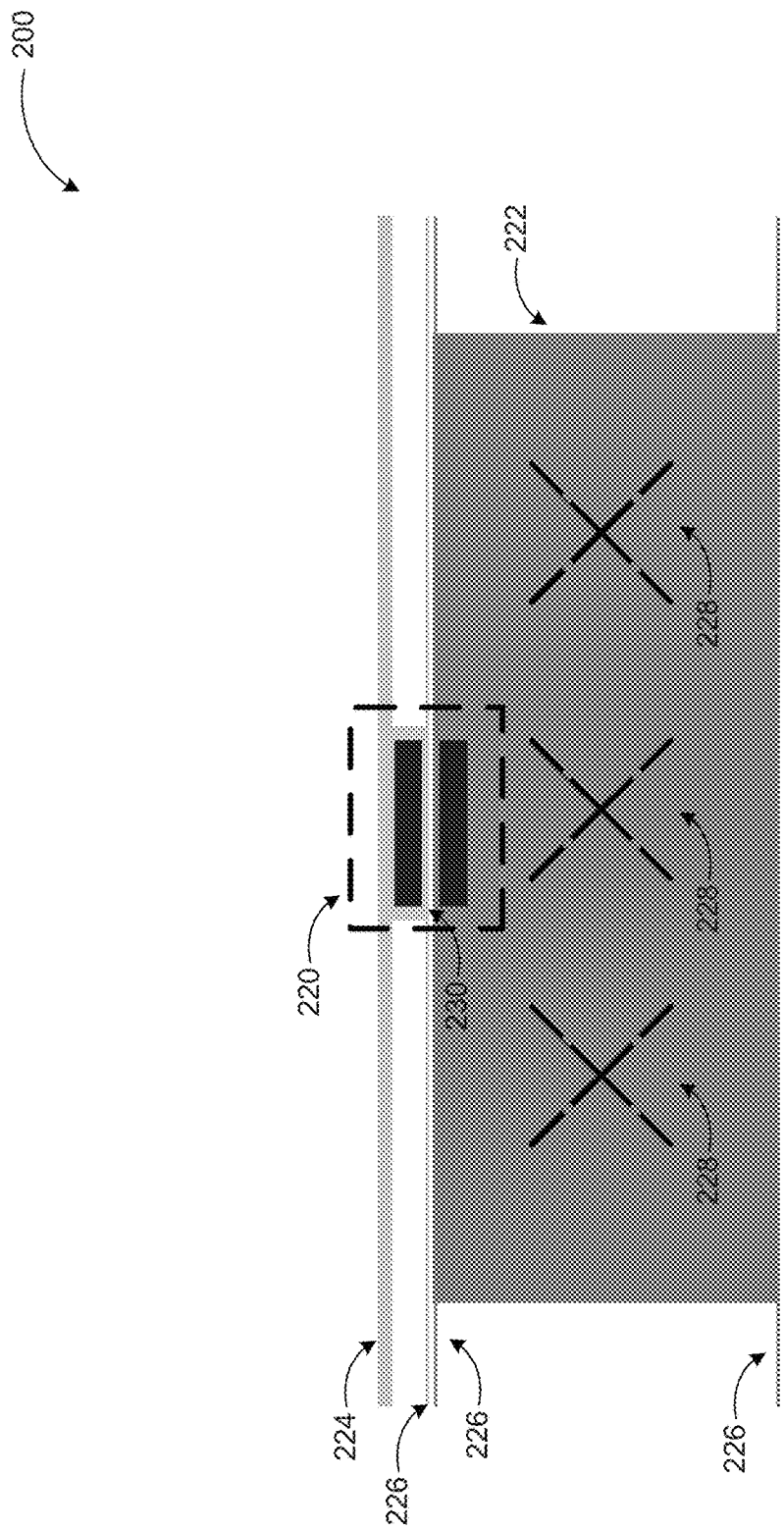
FIG. 2A illustrates an example optomechanical accelerometer.

FIG. 2A illustrates an example optomechanical accelerometer, arranged in accordance with at least some embodiments described herein.

Diagram 200 shows an optomechanical accelerometer device with a test mass structure 222 and nano-tethers 226. A zipper cavity structure 220 including two patterned photonic crystal nanobeams, one attached to the test mass structure 222 and one anchored to the rigid frame 224. The cross-shaped cuts 228 on the test mass structure 222 may facilitate undercutting the device. The cuts may be in any suitable form and number in other embodiments.

A light source for detecting the displacement in the cavity due to acceleration may be in visible, ultraviolet (UV), infrared (IR), and near those optical wavelength ranges. Furthermore, other ranges such as radar wavelengths may be used with meta-material based cavities. In an example scenario, the accelerometer device in diagram 200 may be designed to operate in the telecom band with a measured optical mode resonance at $\lambda_o$=1537 nm and an optical Q-factor of $Q_o$=9500. With the optical cavity field being largely confined to the slot 230 between the nanobeams, the optical resonance frequency may be sensitively coupled to relative motion of the nanobeams in the plane of the accelerometer device. A displacement of the test mass caused by an in-plane acceleration of the supporting microchip may then be read-out optically, where the optical transmission through or reflection from the photonic crystal cavity may be monitored via an evanescently coupled fiber taper waveguide anchored to the rigid side of the cavity, for example. Utilizing a narrow bandwidth (e.g., <300 kHz) laser source, with laser frequency detuned to the red side of the cavity resonance, fluctuations of the resonance frequency due to motion of the test mass may be translated linearly into amplitude fluctuations of the transmitted laser light field in some examples.

Other techniques of coupling light into the zipper cavity structure may include End-Fire coupling with an on-chip tapered waveguide. An optical fiber may be integrated, for example, by gluing into a v-groove with UV epoxy, which may efficiently couple light into a curved waveguide which in turn may couple to the optical resonator on the edge of the test-mass. The waveguide and optics may be supported by horizontal tethers. Further approaches of coupling light into the zipper cavity structure may include, but are not limited to, single-sided evanescent fiber coupling to an on-chip waveguide or free-space grating coupler.

Figure 2B:
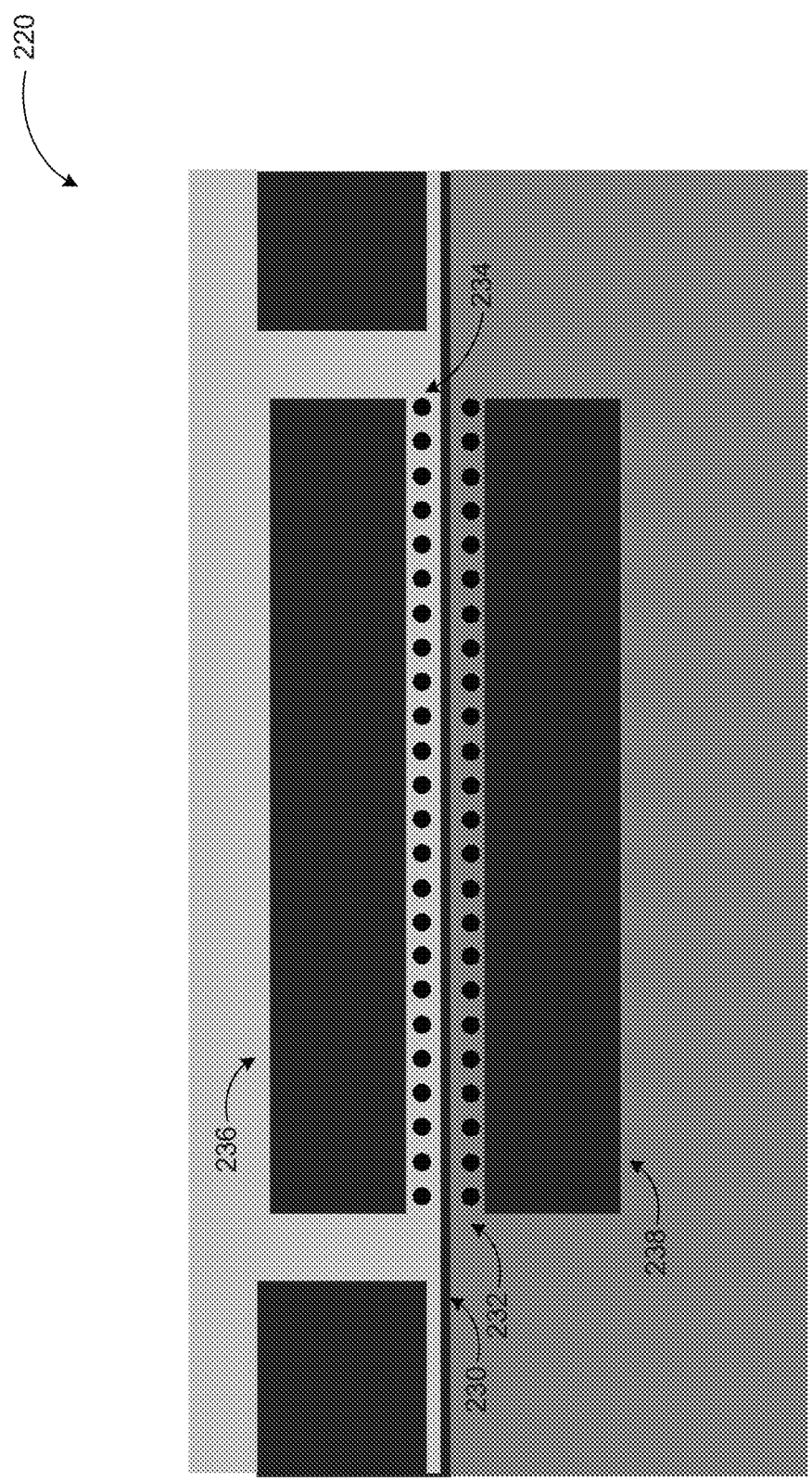
FIG. 2B illustrates the optical cavity region of the example optomechanical accelerometer of FIG. 2A.

FIG. 2B illustrates the optical cavity region of the example optomechanical accelerometer of FIG. 2A, arranged in accordance with at least some embodiments described herein.

The zipper cavity structure 220 of diagram 200 is shown in more detail in FIG. 2B. The zipper cavity structure 220 may include patterned structures 232, 234, 236, and 238 with the slot 230 between two sides of the zipper cavity structure. The slot width may typically be 50-500 nm and the length may range between 10 and 50 microns. This slot width may increase (decrease) as the test-mass moves away from (towards) the rigid side. The top side of the zipper cavity structure may be embedded into the rigid side of the accelerometer while the lower side is embedded into the test mass structure 222. A zipper cavity may be formed by a portion of the test mass and a portion of the frame, each portion including a photonic crystal, the portions being spaced apart and separated by a slot. In some examples, the zipper cavity may include an elongated beam formed in the test mass. In some examples, the zipper cavity may include an elongated beam formed in the frame. An elongated beam formed in the test mass may be generally parallel to an elongated beam formed in the frame, each beam including a photonic crystal, with the beams forming the side walls of a slot structure. A suitable photonic cavity may also be formed from two parallel sides of a two-dimensional photonic crystal separated by a slot gap.

An optomechanical accelerometer according to some embodiments may use a cavity resonant displacement sensor based on a zipper photonic crystal nanocavity to measure the displacement of an integrated test mass generated by an acceleration applied to the chip. In some examples, the cavity-resonant sensor may be fully integrated on-chip and exhibit a displacement resolution on the order of a few fm/rt Hz due to its strong optomechanical coupling.

According to some embodiments, the accelerometer structure may be fabricated in a silicon nitride thin film and constitute a rectangular test mass flexibly suspended on high aspect ratio silicon nitride nano-tethers under high tensile stress. The relatively large mechanical Q-factors may enable reduction of thermomechanical acceleration noise to a level of 1~micro-g/rt-Hz, while keeping a resonance frequency of about 2.7 kHz (and thereby an operation bandwidth up to this frequency) and retaining small sizes.

The performance metrics of an accelerometer according to embodiments may be further enhanced, for example, by reducing the thermal noise floor through increasing the mass while keeping the resonance frequency at a constant high value by controlling the device stiffness (e.g., by adding nano-tethers). The use of many thin tethers to maintain high frequencies in larger mass devices instead of employing the same number of tethers with increased width may maintain the high quality factors in these structures. The use of wider tethers may reduce the mechanical quality factor and thus decrease device performance.

In some examples, relatively small test masses on the order of 10-1000 nanograms may be employed allowing for harnessing radiation-pressure based optical back-action effects, for example for dynamically tuning the resonance frequency (and thereby the sensitivity/resolution) of the accelerometer or for optically damping the structure to avoid ringing effects when the sensor is subjected to a step input.

In other examples, the accelerometer may be fully integrated on-chip and fabricated using micromachining techniques in a single lithography step. The accelerometer may allow for the integration with on-chip waveguide couplers and chip-based readout/calibration electronics. Electrostatic actuators may allow for in-situ tuning of the optical resonance and damping of the mechanical mode enabling closed-loop operation and thereby enhancing the dynamic range. For example, electrostatic actuators may be used to adjust the relative position of the rigid and flexible sides, thus changing the slot gap size. In some examples, an electrostatic potential between electrical conductors in the test mass and in the frame may be adjusted, so as to modify the position of the test mass relative to the frame, for example modifying the slot width.

Figure 2C:
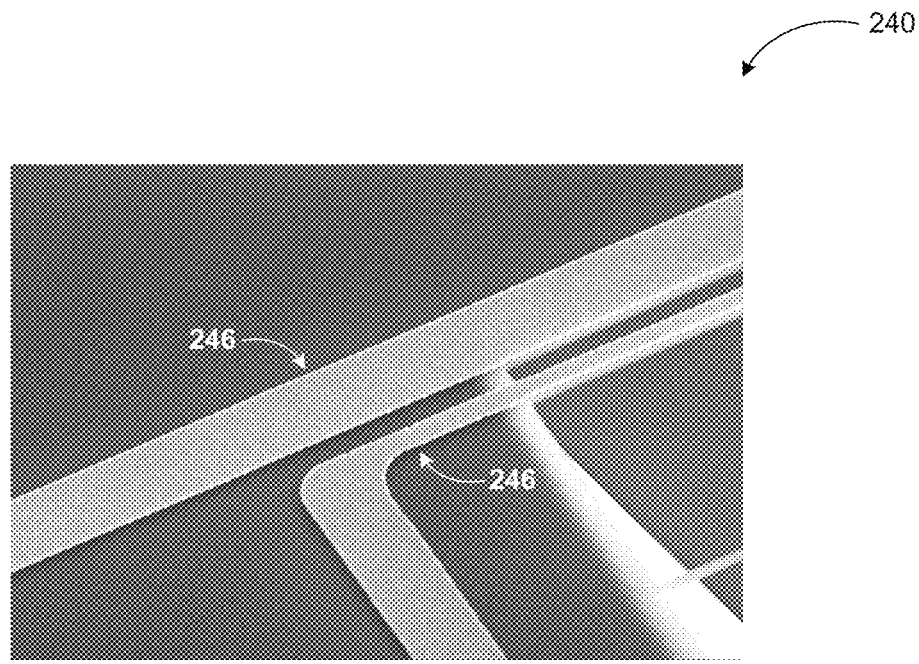
FIG. 2C illustrates details of an accelerometer structure with a focus on capacitive electrodes for tuning the slot gap separation between the two nanobeams.
Figure 2C:
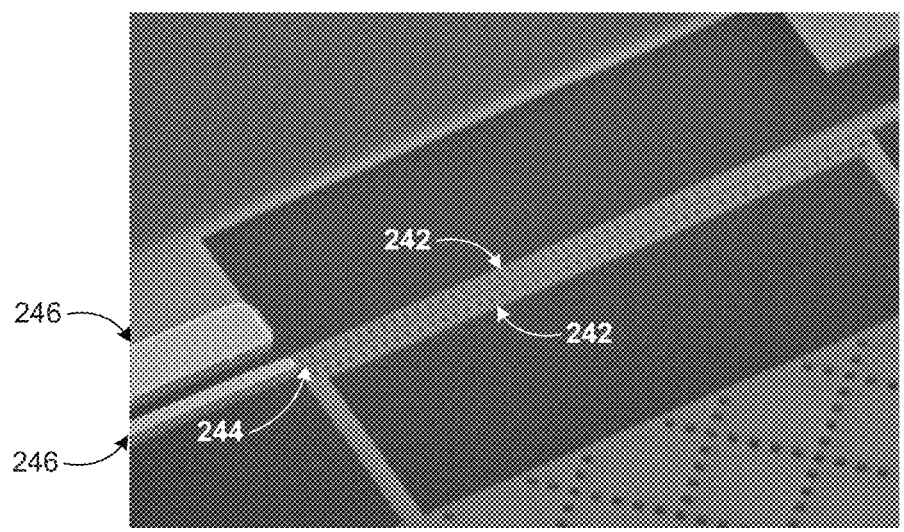

FIG. 2C illustrates details of an accelerometer structure with a focus on capacitive electrodes for tuning the slot gap separation between the two nanobeams, arranged in accordance with at least some embodiments described herein.

As shown in diagram 240, the optical slot 244 is between two individual photonic crystal beams 242. The size of the slot may be adjusted using an electrostatic force generated between pairs of metal wires 246. In some examples, a laser source may be used to insert light into the optical modes of the zipper cavity structure between the two photonic crystal beams 242. The light may be confined in the optical slot region making the optical mode frequency ($\omega_c$) highly sensitive to the separation s of the two beams with an optomechanical coupling of $g'_{OM}=\partial\omega_c/\partial s=\omega_c/L_{OM}$. The electrostatic actuators (i.e. the pairs of contacts with the underlying silicon nitride) may form a capacitance (capacitance C), which may create an electrostatic force $F_{el}=(\frac{1}{2})(dC/dw_g)V_\alpha^2$ when applying a voltage $V_\alpha$ across the capacitor gap $w_g$ (FIG. 2). The capacitor gap is the gap between the two wires 246. $F_{el}$ may lead to contraction of the capacitor gap, thus pulling the "rigid" side of the test mass closer to the frame and increasing the optical slot gap 244 size, thereby, tuning the cavity resonance. The slot width may range between 50 and 500 nm and the slot length may range between 10 and 50 microns in some examples.

Figure 3:
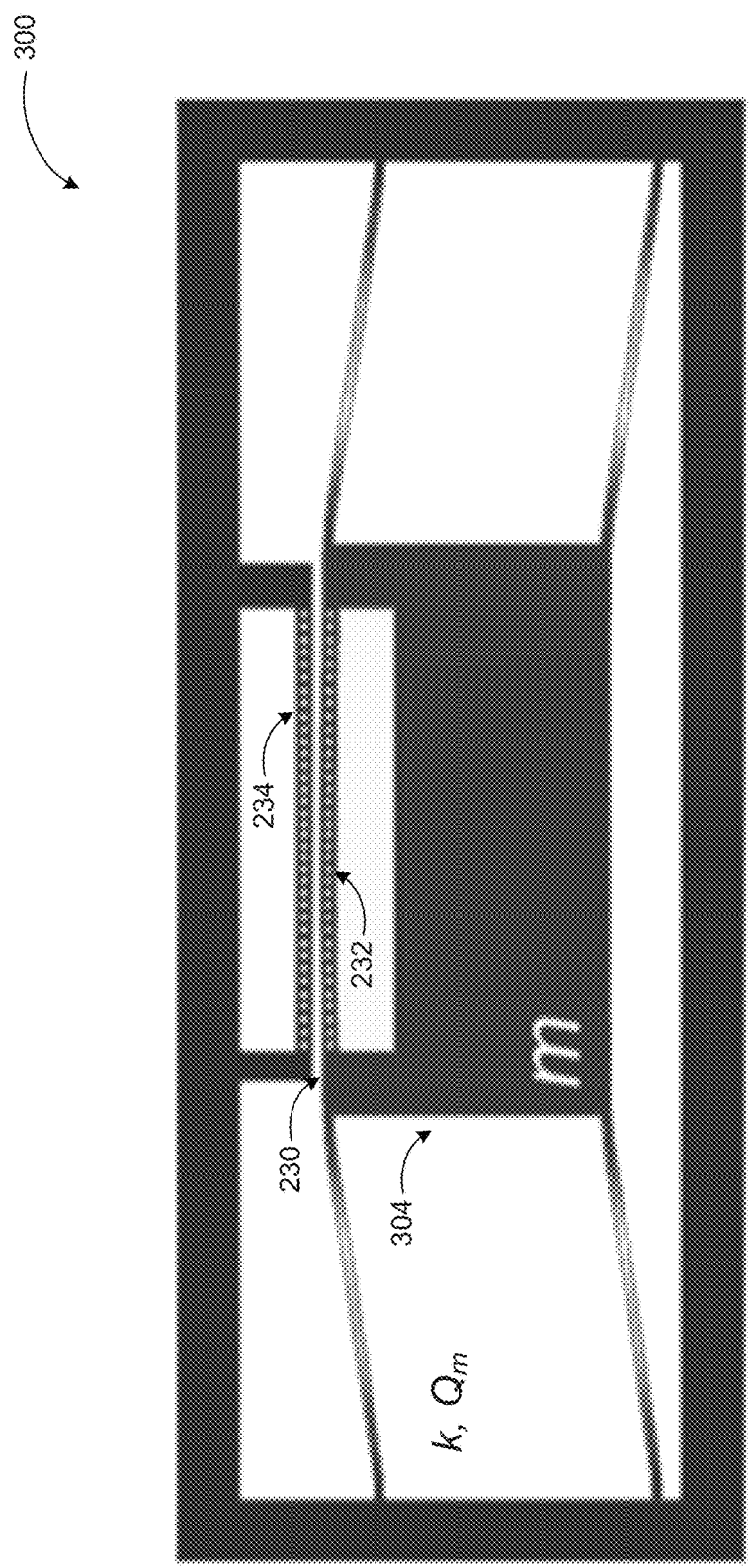
FIG. 3 illustrates schematic displacement profile of the fundamental in-plane mechanical mode used for acceleration sensing in an optomechanical accelerometer such as the example optomechanical accelerometer of FIG. 2A.

FIG. 3 illustrates schematic displacement profile of the fundamental in-plane mechanical mode used for acceleration sensing in an optomechanical accelerometer such as the example optomechanical accelerometer of FIG. 2A, arranged in accordance with at least some embodiments described herein.

The fundamental in-plane mechanical mode of the optomechanical accelerometer structure of FIG. 2A is depicted in diagram 300 with patterned structures 232, 234 of the zipper cavity structure, slot 230 separating the two sides of the zipper cavity structure and test mass structure 304 tethered through nano-tethers. The shading on the different parts of the structure corresponds to a color map representing the mechanical mode's displacement.

In an example scenario, the fundamental in-plane mechanical mode may have a frequency of $f_m=27.5$ kHz with a motional mass of $m=10*10^{-12}$ kg and a mechanical quality factor $Q_m=1.4*10^6$ (in vacuum) resulting in an estimated thermal noise $a_{th}=1.4$ μg/Hz$^{1/2}$.

Figure 4:
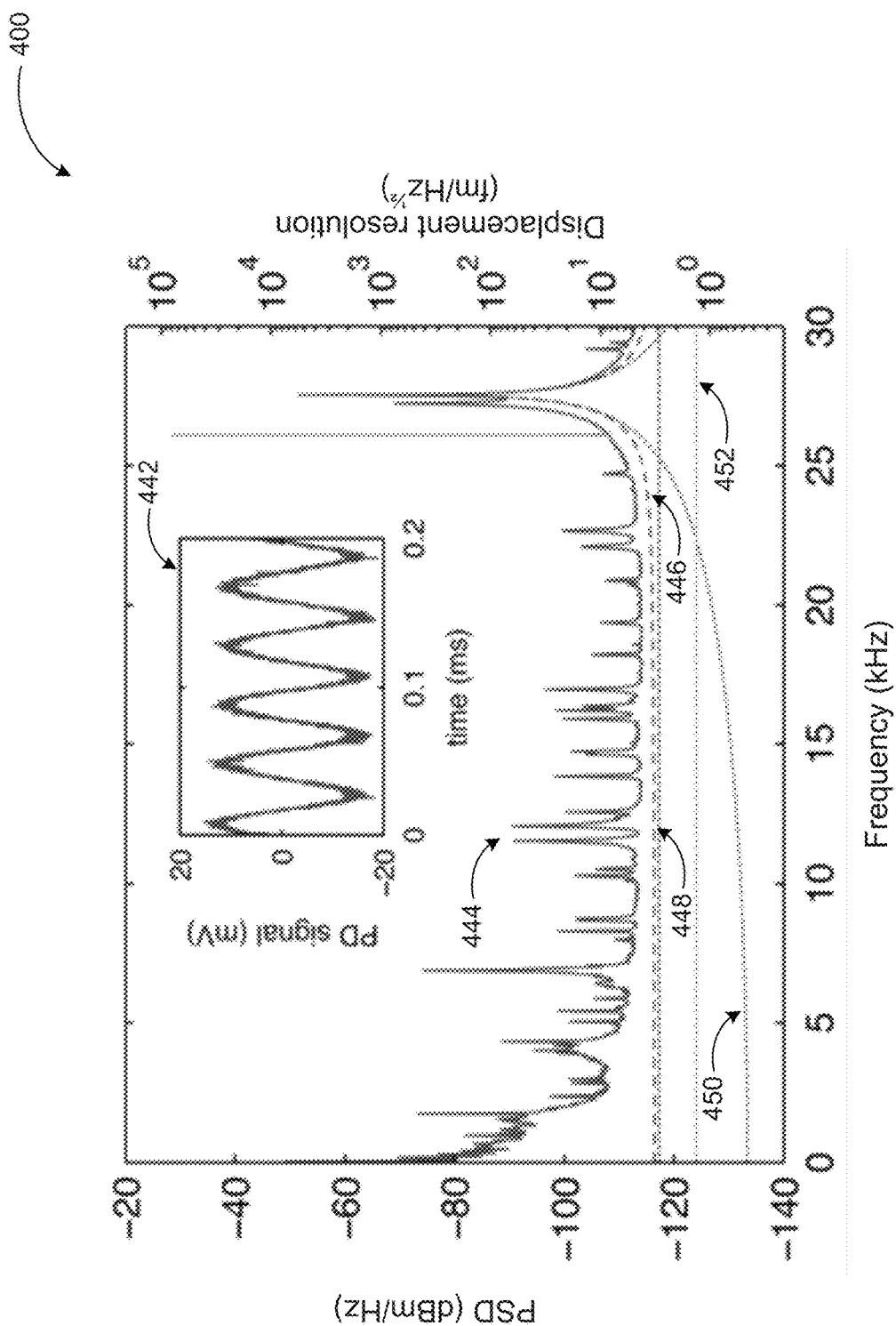
FIG. 4 illustrates an optical power spectral density (PSD) plot of a balanced photo-detector (BPD) signal from an optomechanical accelerometer showing mechanical modes at 27.5 kHz and an equivalent displacement noise comparing various noise types and a total of all noise contributions to the BPD signal.

FIG. 4 illustrates an optical power spectral density (PSD) plot of a balanced photo-detector (BPD) signal from an optomechanical accelerometer showing mechanical modes at 27.5 kHz and an equivalent displacement noise comparing various noise types and a total of all noise contributions to the BPD signal, arranged in accordance with at least some embodiments described herein.

The PSD plot 400 shows a time trace of the transduction of an example applied acceleration of 35.6 mg at 25 kHz (442). Curve 444 represents the electronic PSD of the optically transduced signal obtained from an accelerometer such as the accelerometer of FIG. 2A. For the example results, the cavity may be driven with an incident laser power of $P_{in}$=116 mW, yielding an intracavity photon number of ≈430. The two peaks around 27.5 kHz may arise from thermal Brownian motion of the fundamental in- and out-of-plane mechanical eigenmodes of the suspended test mass.

The transduced signal level of the fundamental in-plane resonance, the mode used for acceleration sensing, may be consistent with an optomechanical coupling constant of $g_{OM}$=2π*5.5 GHz/nm, where $g_{OM}$=$d\omega_o$/dx may be defined as the optical cavity frequency shift per unit displacement. The curve 450 depicts the theoretical thermal noise background of this mode. The series of sharp features between zero frequency (DC) and 15 kHz may be due to mechanical resonances of the anchored fiber-taper. The noise background level in PSD plot 400 is dominated by photon shot-noise, an estimate of which is indicated by the curve 448. The curve 452 corresponds to the electronic photodetector noise, and the curve 446 represents the sum of all noise terms. The broad noise at lower frequencies may arise from fiber-taper motion and acoustic pick-up from the environment. The right hand axis in FIG. 4 quantifies the optically transduced PSD in units of equivalent transduced displacement amplitude of the fundamental in-plane mode of the test mass, showing a measured shot-noise-dominated displacement imprecision of about 4 fm/Hz$^{1/2}$. A balanced detection scheme may allow for efficient rejection of laser amplitude noise, yielding shot noise limited detection for frequencies above approximately 1 kHz.

In an example configuration, a laser tight may be used to probe the zipper cavity motion and split with a beam splitter. The signal arm may be sent through a fiber polarization controller (FPC) and a fiber taper, which may be coupled to the optical cavity, while the other arm may be sent directly to a balanced photo-detector (BPD). Variable optical attenuators (VOA) in each arm may balance the powers, and a power meter (PM) may be used to calibrate the probe power. The BPD signal may be sent to a proportional-integral controller (PI) locking the laser half a line width red-detuned from the optical resonance. Transduced accelerations may be measured using either an electronic spectrum analyzer (ESA) or a lock-in amplifier.

Figure 5:
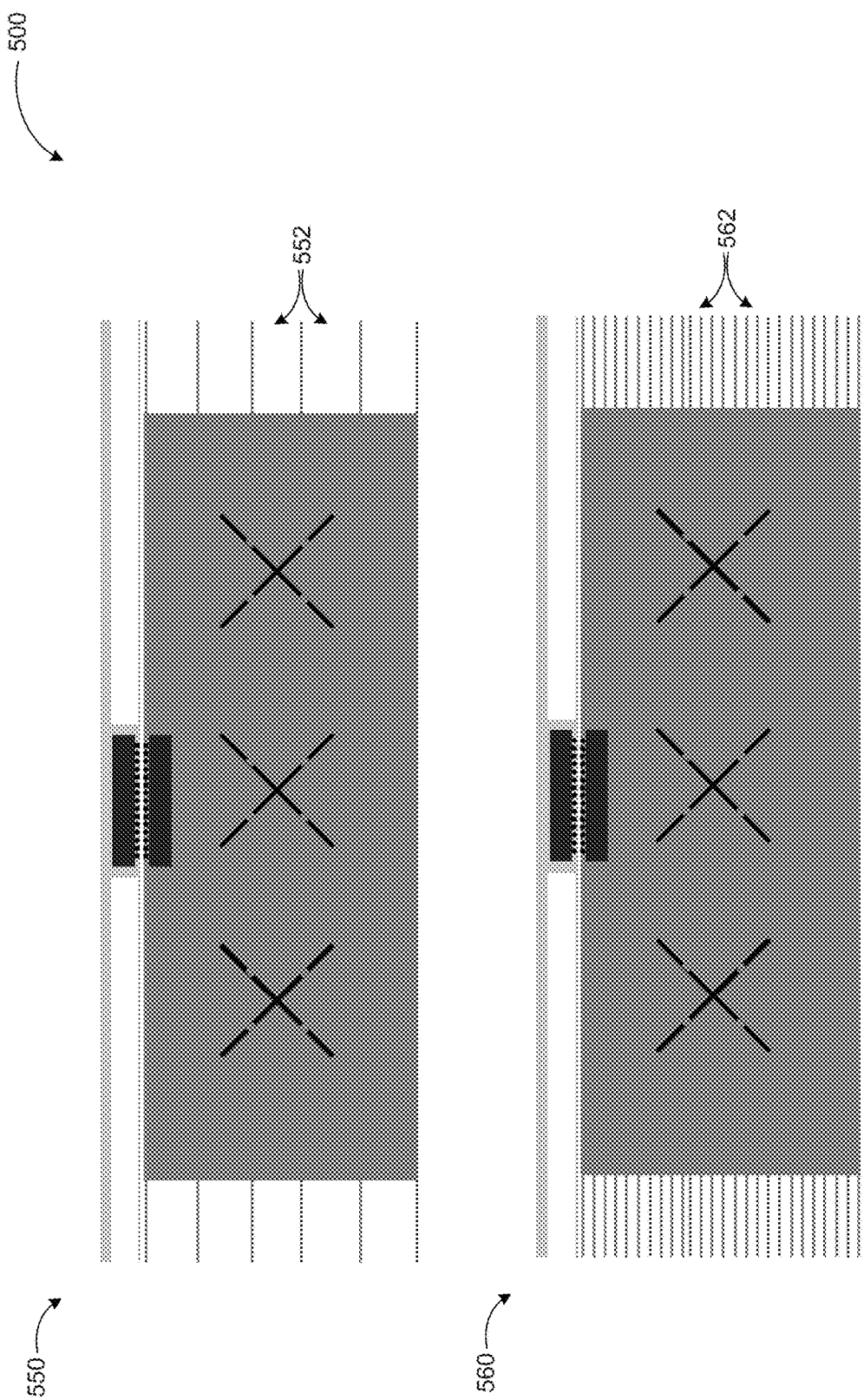
FIG. 5 illustrates two example optomechanical accelerometers with different number of tethers and, thereby, resonance frequencies.

FIG. 5 illustrates two example optomechanical accelerometers with different tethers and, thereby, resonance frequencies, arranged in accordance with at least some embodiments described herein.

Diagram 500 shows two example versions of the accelerometer device of FIG. 2A with increased number of tethers coupled to the test mass structure. Example accelerometer 550 includes 12 tethers 552 and example accelerometer 560 includes 42 tethers 562.

Adding mass alone may result in a reduction of the sensor bandwidth. However, by scaling a number of nano-tether suspensions with the test mass size the bandwidth may be maintained substantially constant. Moreover, adding nano-tethers may not result in a degradation of the mechanical Q-factor. Thus, a size of the test mass structure and a number of the nano-tethers may be adjusted independently or simultaneously. For example, simultaneously scaling the width of the test mass and the number of nano-tethers by a factor of 100 on the example accelerometer device shown in FIG. 2A, may reduce the thermal noise-equivalent acceleration (NEA) tenfold or more.

The resolution of an accelerometer may be quantified by a noise-equivalent acceleration (NEA), which may be defined as the square root of the sum of the squares of thermal noise due to Brownian motion ($a_{th}$), displacement readout noise ($a_{det}$) due to the photo detector, and added noise (back-action) onto the test mass due to the act of measurement ($a_{add}$).

To minimize the NEA, the intrinsic thermal noise may be reduced, which involves maximizing the mass-Q product at a given $\omega_m$. In conventional accelerometers, the Q-factor is relatively low, which demands large test masses for high resolution. In contrast, in the zipper cavity structure based accelerometer devices according to some embodiments may use nano-tether suspension of a nanogram test mass to yield high intrinsic mechanical Q-factors (1~2*10$^6$) and strong thermo-optomechanical back-action to damp and cool the thermal motion of the test mass.

Figure 6:
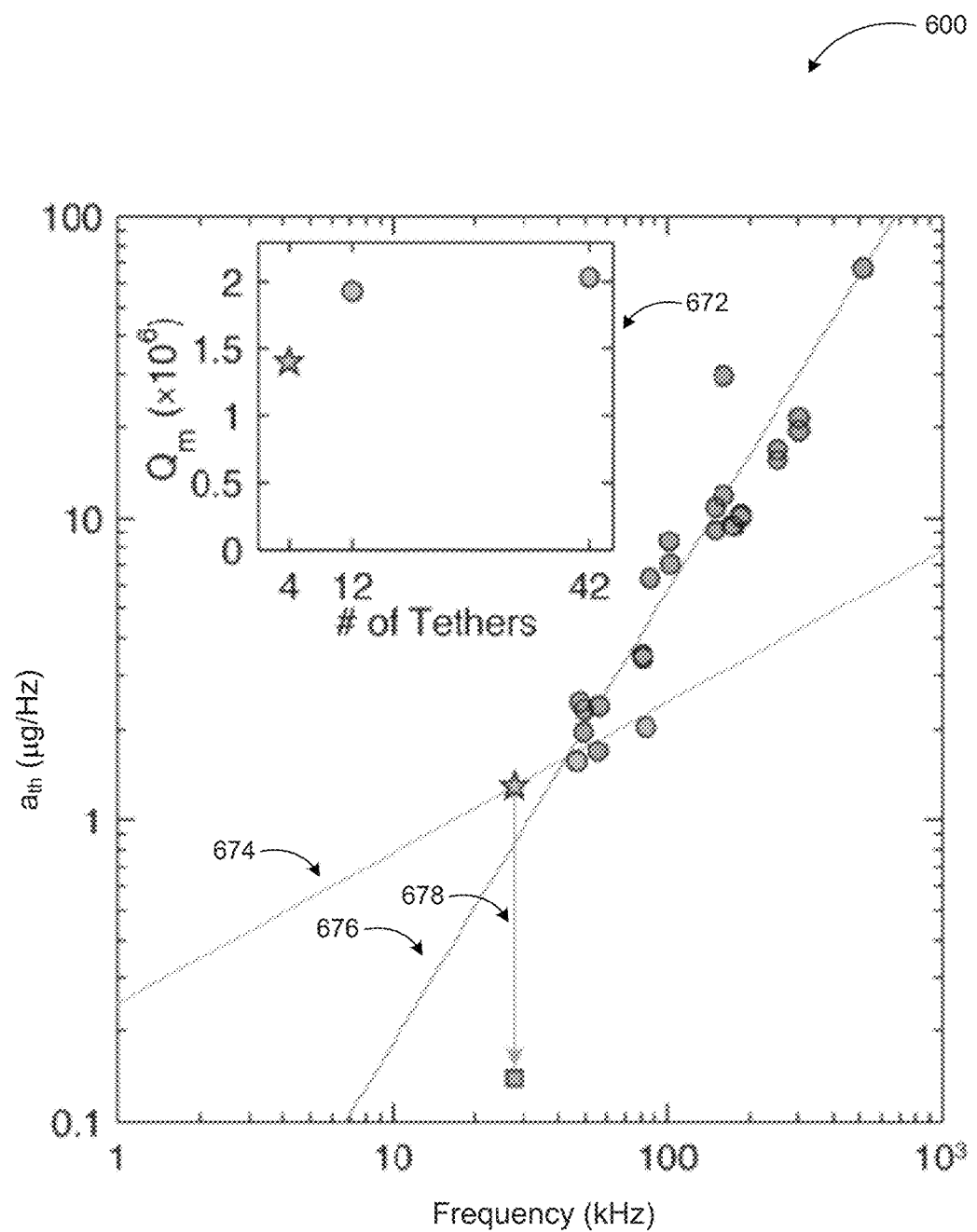
FIG. 6 illustrates thermal acceleration noise density of fabricated optomechanical accelerometers with varying numbers of tethers and test mass sizes, including the accelerometers in FIG. 5.

FIG. 6 illustrates thermal acceleration noise density of the two example optomechanical accelerometers of FIG. 5, arranged in accordance with at least some embodiments described herein.

Diagram 600 depicts a calculated $a_{th}$ versus the mechanical frequency of a number of example accelerometer devices in curve 676. Curve 676 is obtained by adding mass with fixed $Q_m$ and spring constant k, while the curve 674 is obtained by varying k while keeping $Q_m$ and m fixed. Varying both m and k may allow for independent control of bandwidth and resolution, for example along the line 678, where the ratio k/m is constant. The inset 672 shows $Q_m$ for the accelerometer devices along the curve 676 versus number of nano-tethers attached to the test mass.

Accelerometer devices according to some embodiments may be formed from a silicon chip and allow for the integration of electrostatic tuning-capacitors, fiber-coupled on-chip waveguides, and on-chip electronics, which enable convenient, small form-factor packaging and may eliminate a need for expensive tunable lasers. In addition, nanoscale optomechanical cavities may offer a resource of strong radiation pressure back-action. The optical spring effect, for example, may allow for dynamic tuning of the mechanical resonance frequency, which may increase the low-frequency displacement response (inverse quadratically with frequency) and decrease thermal noise (with the square root of frequency). Moreover, back-action cooling may provide a resource to damp the response of the oscillator without compromising the resolution.

According to some embodiments, an accelerometer structure may be constructed in an about 400 nm thick silicon nitride (SiN) layer formed on top of an about 500 mm thick single-crystal silicon wafer. The SiN may be stoichiometric and may be grown in low-pressure chemical vapor deposition (LPCVD) under conditions that allow for large internal tensile stress (e.g., ranging between about 0.5 and about 10 GPa). The accelerometer structures comprising the test mass, the support nano-tethers, and the zipper cavity may be formed in a single electron-beam lithography step. The mask may be transferred into the SiN layer using inductively coupled plasma/reactive-ion etching (ICP/RIE) dry etching in a SF6=C4F8 plasma, for example. Resist residues may be removed in a combination of heated Microposit 1165 remover and Piranha solution (3:1 $H_2SO_4$:$H_2O_2$) at 120° C. The structures may be undercut by anisotropic wet-etching in 70° C. hot KOH and cleaned in a second Piranha etching step. Critical point dying in $CO_2$ may avoid collapsing of the zipper cavities.

Figure 7:
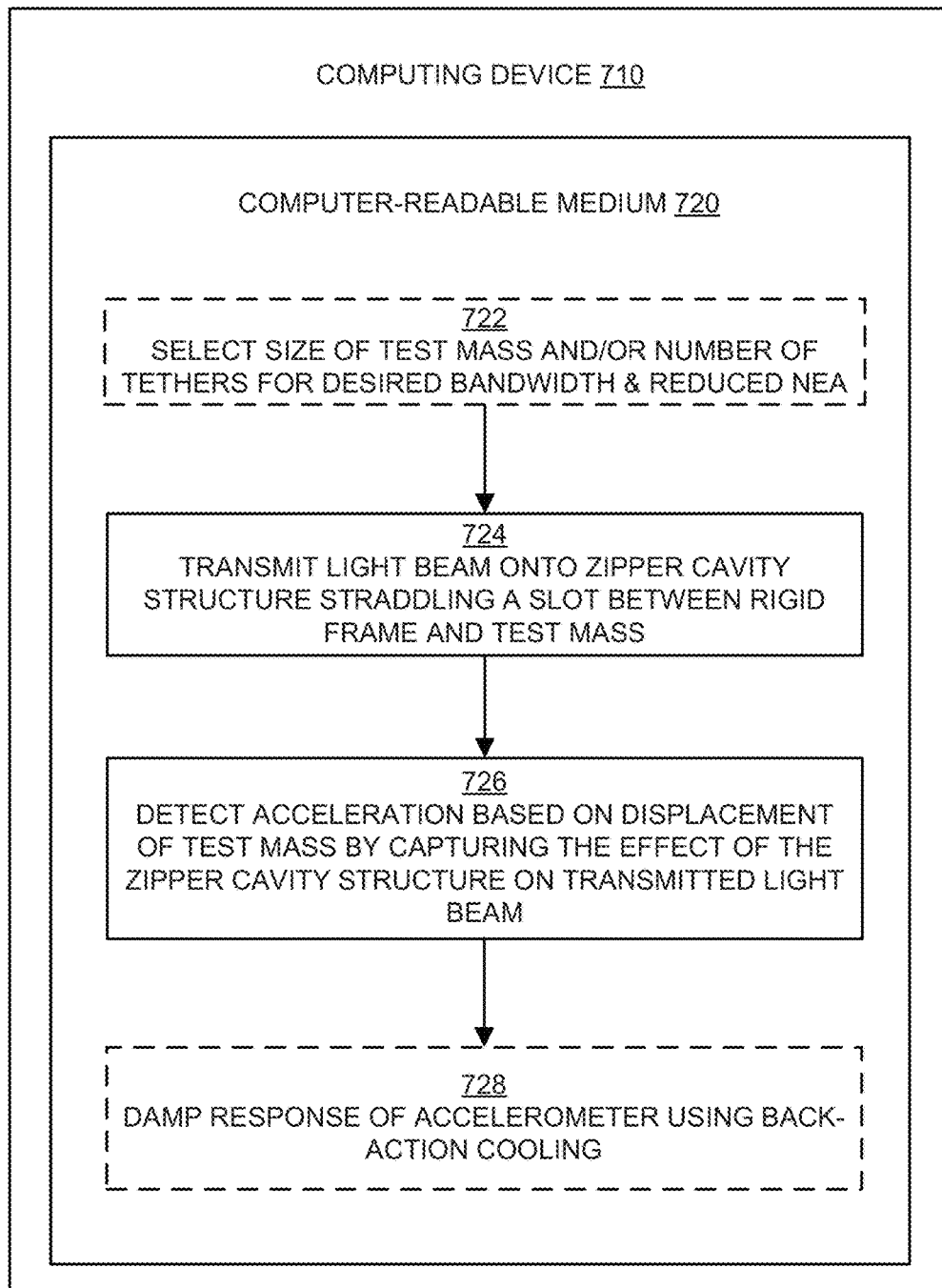
FIG. 7 is a flow diagram illustrating an example method for operating an optomechanical accelerometer.

FIG. 7 is a flow diagram illustrating an example method for operating an optomechanical accelerometer arranged in accordance with at least some embodiments described herein.

Example methods may include one or more operations, functions or actions as illustrated by one or more of blocks 722, 724, 726, and/or 728, and may in some embodiments be performed on an accelerometer device such as the accelerometer device in FIG. 2A. The operations described in the blocks 722-728 may also be stored as computer-executable instructions in a computer-readable medium such as a computer-readable medium 720 of a computing device 710.

An example process for operating an optomechanical accelerometer may begin at optional block 722, "SELECT SIZE OF TEST MASS AND/OR NUMBER OF TETHERS FOR DESIRED BANDWIDTH & REDUCED NEA", where a size (and thereby the mass) of the test mass structure 222 and/or a number of nano-tethers 226 connecting the test mass to the rigid frame 224 may be selected for a desired operating frequency (thereby the bandwidth) and reduced noise-equivalent acceleration.

Optional block 722 may be followed by block 724, "TRANSMIT LIGHT BEAM ONTO ZIPPER CAVITY STRUCTURE STRADDLING A SLOT BETWEEN RIGID FRAME AND TEST MASS", where a focused light beam such as a laser beam may be transmitted onto the zipper cavity structure 220 symmetrically formed on either side of a slot between the test mass structure 222 and the rigid frame 224. The accelerometer structure (including the zipper cavity structure, the test mass, and the nano-tethers) may be integrated into a single MEMS device along with the light source in some embodiments.

Block 724 may be followed by block 726, "DETECT ACCELERATION BASED ON DISPLACEMENT OF TEST MASS BY CAPTURING THE EFFECT OF THE ZIPPER CAVITY STRUCTURE ON TRANSMITTED LIGHT BEAM", a photo detector may capture reflected or transmitted light from the zipper cavity structure and detect the displacement of the test mass corresponding to the acceleration imposed on the entire structure. The photo detector may also be an integrated part of the MEMS device.

Block 726 may be followed by optional block 728, "DAMP RESPONSE OF ACCELEROMETER USING BACK-ACTION COOLING", where a response characteristic of the accelerometer device may be damped through back-action cooling further reducing NEA and enhancing dynamic range of the accelerometer.

Figure 8:
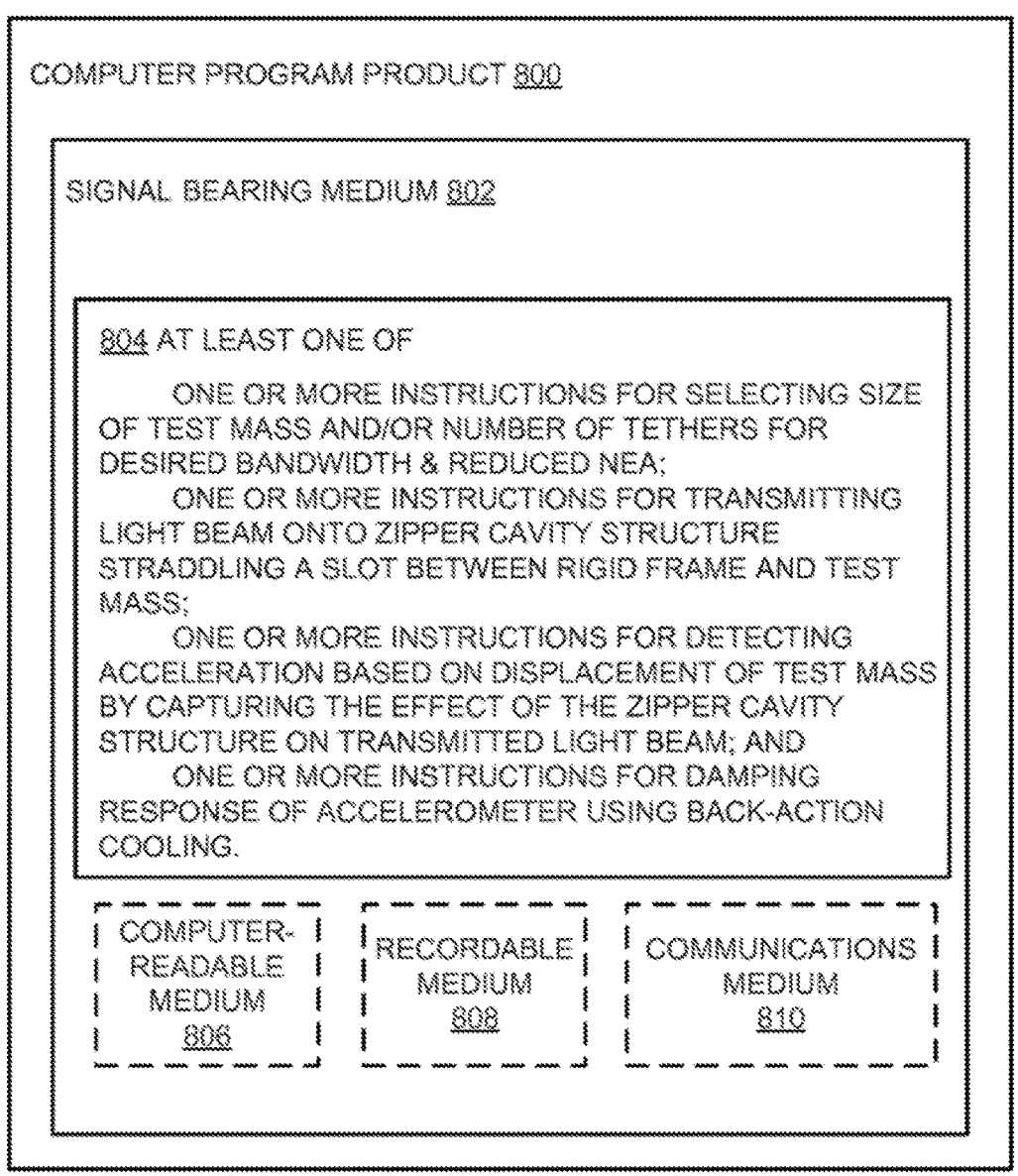
FIG. 8 illustrates a block diagram of an example computer program product, all arranged in accordance with at least some embodiments described herein.

FIG. 8 illustrates a block diagram of an example computer program product arranged in accordance with at least some embodiments described herein.

In some examples, as shown in FIG. 8, the computer program product 800 may include a signal bearing medium 802 that may also include one or more machine readable instructions 804 that, when executed by, for example, an accelerometer device may provide the functionality described herein. Thus, for example, referring to the accelerometer of FIG. 2A, a MEMS device that includes the accelerometer may undertake one or more of the tasks shown in FIG. 8 in response to the instructions 804 conveyed by the signal bearing medium 802 to perform actions associated with acceleration detection through an optomechanical accelerometer as described herein. Some of those instructions may include, for example, selecting size of test mass and/or number of tethers for desired bandwidth & reduced NEA, transmitting light beam onto zipper cavity structure straddling a slot between rigid frame and test mass, detecting acceleration based on displacement of test mass by capturing the effect of the zipper cavity structure on transmitted light beam, and damping response of accelerometer using back-action cooling, according to some embodiments described herein.

In some implementations, the signal bearing medium 802 depicted in FIG. 8 may encompass a computer-readable medium 806, such as, but not limited to, a hard disk drive, a solid state drive, a Compact Disc (CD), a Digital Versatile Disk (DVD), a digital tape, memory, etc. In some implementations, the signal bearing medium 802 may encompass a recordable medium 808, such as, but not limited to, memory, read/write (R/W) CDs, R/W DVDs, etc. In some implementations, the signal bearing medium 802 may encompass a communications medium 810, such as, but not limited to, a digital and/or an analog communication medium (e.g., a fiber optic cable, a waveguide, a wired communications link, a wireless communication link, etc.). Thus, for example, the computer program product 800 may be conveyed to one or more modules of the processor by an RF signal bearing medium, where the signal bearing medium 802 is conveyed by the wireless communications medium 810 (e.g., a wireless communications medium conforming with the IEEE 802.11 standard).

Alternative Configurations:

The use of material with large in-plane stress according to embodiments increases the mechanical frequencies and the mechanical Q-factor. In some examples, a single test mass may be used to detect in-plane and out-of-plane motion, as these have different frequency modes. Alternatively, orthogonal devices may provide three-dimensional motion sensing. In yet another approach, the test mass may be configured to define photonic (zipper) cavities in different planes. Examples include a chip-scale optomechanical accelerometer device, comprising a rigid frame, a test mass; a one or more nano-tethers coupling the test mass to the rigid frame; and a zipper cavity structure formed by a portion of the test mass and an adjacent portion of the frame. In this context, a chip-scale accelerometer is of a size that may be integrated on-chip, for example with supporting electronic circuit components, and/or with other accelerometers. For example, the frame may have a lateral dimension in the plane of the chip that is greater than 3 microns up to the extent of the chip. The frame may be rigid in that motion of the test mass is effectively due entirely to motion of the tethers, and test mass motion due to acceleration-induced frame distortion may be neglected. An accelerometer may be integrated on-chip with supporting electronic circuitry for signal processing, or otherwise used with an electronic circuit operable to determine acceleration or properties derived therefrom (such as displacement, motion detection, energy expenditure, frequency, frequency change, and the like).

A further approach may include a piezoelectric transducer to induce vibration. Changes in resonance frequency may then be sensitively detected, allowing monitoring of ambient conditions, changes in properties of surrounding fluidic media, analyte adhesion to the test mass, and comparable environments. Furthermore, electric fields may be used to tune the cavity. For example, electric fields may be generated using conducting tethers to stabilize the test mass. Fields may be electromagnetically induced in isolated electrodes. A piezoelectric element may be used to adjust test mass or beam position(s), exert additional force on a tether, etc. The structure may also be composed out of other highly-stressed (e.g., ~1 GPa) optically transparent thin-film materials such as Aluminum Nitride.

Example Application Environments:

Accelerometers may have multiple applications in industry and science. For example, highly sensitive accelerometers may be used as components of inertial navigation systems for aircraft and missiles. Accelerometers may also be used to detect and monitor vibration in rotating machinery. In more recent past, accelerometers are used increasingly in tablet computers, smart phones, and digital cameras for image stability and as an input mechanism.

Further example applications may include measurement of vehicle acceleration and vibration. Similarly, vibration may be measured using an accelerometer on machines, buildings, process control systems and/or safety installations. Furthermore, seismic activity, inclination, machine vibration, dynamic distance and speed with or without the influence of gravity may be measured using accelerometers.

In biology, accelerometers may be used to detect movement of animals (as well as humans) and allow study of behavioral patterns in native environments without the need for visual observation. Examples include exercise monitoring equipment using an accelerometer as described. Further, but not exhaustive, examples of use for accelerometers may include human activities—walking, running, dancing or skipping; working machines—inside a building or in the surrounding area; construction—driving piles, demolition, drilling and excavating; moving loads on bridges; vehicle collisions; impact loads—falling debris; concussion loads—internal and external explosions; collapse of structural elements; wind loads and wind gusts; air blast pressure; and comparable ones.

According to some examples, an optomechanical accelerometer device may be provided. An optomechanical accelerometer device may include a frame, a test mass, a plurality of nano-tethers coupling the test mass to the frame, and a zipper cavity structure formed by a portion of the test mass and an adjacent portion of the frame.

According to other examples, the zipper cavity structure may be formed by a photonic crystal in the test mass and a second photonic crystal in the frame, separated by a slot. The nano-tethers may be configured to provide elongated mechanical support. The zipper cavity structure may include two patterned photonic crystal nanobeams, one of the nanobeams formed within the test mass and another of the nanobeams formed within the frame.

According to further examples, the accelerometer device may also include a fiber taper waveguide anchored to the frame in a vicinity of the zipper cavity structure, where the waveguide is configured to couple a light beam to the zipper cavity structure monitor the photonic crystal nanobeams for detecting a displacement of the test mass caused by an in-plane acceleration of the frame. At least one of a size of the test mass and/or a number of the nano-tethers may be selected such that a noise-equivalent acceleration (NEA) of the accelerometer device is reduced and a mechanical quality factor of the device is increased. The size of the test mass and/or the number of the nano-tethers may also be selected such that an operational bandwidth of the accelerometer device is substantially maintained.

According to yet other examples, the accelerometer device may be fabricated in a silicon nitride thin film. The accelerometer device may be integrated into a microelectromechanical system (MEMS) device. The test mass may include one or more cuts to facilitate undercutting the accelerometer device, where the cuts may be cross-shaped and substantially evenly distributed on the test mass. A response characteristic of the accelerometer device may be damped through back-action cooling. A sensor bandwidth may be controlled by an optical spring effect and an effective temperature of the sensor may be controlled by one of passive damping and feedback cold-damping. Moreover, one or more electrostatic actuators may be used for in-situ tuning of an optical resonance of the zipper cavity structure and damping of a mechanical mode of the zipper cavity structure to enable closed-loop operation. The accelerometer device may be fabricated in a single lithography step.

According to other examples, an optical microelectromechanical system (OMEMS) device for detecting acceleration may be provided. An example OMEMS device may include an optomechanical accelerometer with a frame, a test mass, a plurality of nano-tethers coupling the test mass to the frame, and a zipper cavity structure formed by a portion of the test mass and an adjacent portion of the frame. The OMEMS device may further include an optical beam source configured to direct a light beam onto the zipper cavity structure and an optical detector configured to detect a displacement of the test mass caused by an in-plane acceleration of the frame.

According to some examples, the optical detector may be configured to detect the displacement of the test mass based on a variation of light transmission through or reflection from the zipper cavity structure. The zipper cavity structure may include two patterned photonic crystal nanobeams and a slot, one of the nanobeams formed as a portion of the test mass and another of the nanobeams formed as a portion of the frame, the nanobeams being separated by the slot. The MEMS device may further include a fiber taper waveguide coupled to the optical detector and anchored to the frame in a vicinity of the zipper cavity structure to receive light transmitted through or reflected from the nanobeams.

According to further examples, at least one of a size of the test mass and/or a number of the nano-tethers may be selected such that a noise-equivalent acceleration (NEA) of the accelerometer device is reduced and a mechanical quality factor of the device is increased. The size of the test mass and/or the number of the nano-tethers may also be selected such that an operational bandwidth of the accelerometer device is substantially maintained. The accelerometer device may be fabricated in a silicon nitride thin film, where the test mass may include one or more out to facilitate undercutting the accelerometer device. A response characteristic of the accelerometer device may be damped through back-action cooling.

According to yet other examples, the MEMS device may further include one or more electrostatic actuators for in-situ tuning of an optical resonance of the zipper cavity structure and damping of a mechanical mode of the zipper cavity structure to enable closed-loop operation. The MEMS device may also include a beam splitter configured to split the light beam, transmit a first portion of the split light beam through the zipper cavity structure, and transmit a second portion of the split light beam to the optical detector as a reference light beam. The optical beam source may be a laser source providing a laser beam and the optical detector may be a balanced photo detector (BPD). The MEMS device may further include a proportional-integral (PI) controller coupled to the optical detector, the PI controller configured to lock the laser beam half a line width red-detuned from an optical resonance of the zipper cavity structure. The MEMS device may also include one or more variable optical attenuators to balance optical beam power.

According to further examples, a method for operating an optomechanical accelerometer device may be provided. An example method may include transmitting a light beam through a zipper cavity structure of the accelerometer device, where the accelerometer device includes a frame, a test mass, a plurality of nano-tethers coupling the test mass to the frame, and the zipper cavity structure formed by a portion of the test mass and an adjacent portion of the frame. The method may further include detecting a displacement of the test mass caused by an in-plane acceleration of the frame by monitoring an effect of the zipper cavity structure on the transmitted light beam.

According to some examples, transmitting the transmitted light beam through the zipper cavity structure may include transmitting the light beam through a fiber taper waveguide anchored to the frame onto two patterned photonic crystal nanobeams, one of the nanobeams formed within the test mass and another of the nanobeams formed within the frame. The method may also include damping a response characteristic of the accelerometer device through back-action cooling. The method may further include employing one or more electrostatic actuators for in-situ tuning of an optical resonance of the zipper cavity.

According to yet other examples, a method for fabricating an optomechanical accelerometer device may be provided. An example method may include forming a mask for accelerometer structures comprising a test mass, support nano-tethers, and a zipper cavity structure and transferring the mask into a silicon nitride layer formed on a single-crystal silicon wafer.

According to further examples, the method may further include forming the accelerometer structures in a single electron-beam lithography step and/or growing the silicon nitride layer using low-pressure chemical vapor deposition (LPCVD) under conditions that enable large internal tensile stress. The nano-tethers may be formed with an about 800 MPa internal tensile stress. The silicon nitride layer may be about 400 nm thick and the silicon wafer may be about 500 µm thick. Transferring the mask into the silicon nitride layer may include dry etching by inductively coupled plasma/reactive-ion etching (ICP/RIE). The method may further include undercutting the accelerometer structures employing anisotropic wet-etching and/or preventing a collapse of the zipper cavity structure employing critical point drying in $CO_2$.

There is little distinction left between hardware and software implementations of aspects of systems; the use of hardware or software is generally (but not always, in that in certain contexts the choice between hardware and software may become significant) a design choice representing cost vs. efficiency tradeoffs. There are various vehicles by which processes and/or systems and/or other technologies described herein may be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations. It will be understood by those within the art that each function and/or operation within such block diagrams, flowcharts, or examples may be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, may be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof and that designing the circuitry and/or writing the code for the software and/or firmware would be well within the skill of one of skill in the art in light of this disclosure.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Versatile Disk (DVD), a digital tape, a computer memory, a solid state drive, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein may be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity of gantry systems; control motors for moving and/or adjusting components and/or quantities).

A typical data processing system may be implemented utilizing any suitable commercially available components, such as those typically found in data computing/communication and/or network computing/communication systems. The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermediate components. Likewise, any two components so associated may also be viewed as being "operably connected", or "operably coupled", to each other to achieve the desired functionality, and any two components capable of being on associated may also be viewed as being "operably couplable", to each other to achieve the desired functionality. Specific examples of operably couplable include but are not limited to physically connectable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicit recited, those skilled in the art will recognize that such recitation should be interpreted to mean at least the recited number (e.g., the bare recitation of "two recitations," without other modifiers, means at least two recitations, or two or more recitations).

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. An optomechanical accelerometer device, comprising:
a frame;
a test mass;
a plurality of nano-tethers coupling the test mass to the frame; and
a zipper cavity structure formed by a portion of the test mass and an adjacent portion of the frame.

2. The optomechanical accelerometer device of claim 1, wherein the zipper cavity structure is formed by a photonic crystal in the test mass and a second photonic crystal in the frame, separated by a slot.

3. The optomechanical accelerometer device of claim 1, wherein the plurality of nano-tethers are configured to provide elongated mechanical support and have a thickness between approximately 100 nm and approximately 500 nm.

4. The optomechanical accelerometer device of claim 1, further comprising a fiber taper waveguide anchored to the frame in a vicinity of the zipper cavity structure, wherein the waveguide is configured to couple a light beam to the zipper cavity structure to monitor photonic crystal nanobeams to detect a displacement of the test mass caused by an in-plane acceleration of the frame.

5. The optomechanical accelerometer device of claim 1, wherein at least one of a size of the test mass and a number of the nano-tethers is selected such that a noise-equivalent acceleration (NEA) of the optomechanical accelerometer device is reduced and a mechanical quality factor of the optomechanical accelerometer device is increased, wherein the at least one of the size of the test mass and the number of the nano-tethers is selected such that an operational bandwidth of the optomechanical accelerometer device is substantially maintained.

6. The optomechanical accelerometer device of claim 1, wherein the optomechanical accelerometer device is integrated into a microelectromechanical system (MEMS) device.

7. The optomechanical accelerometer device of claim 1, wherein the test mass includes one or more cross-shaped cuts to facilitate undercutting the optomechanical accelerometer device.

8. The optomechanical accelerometer device of claim 1, wherein a response characteristic of the optomechanical accelerometer device is damped through back-action cooling.

9. The optomechanical accelerometer device of claim 1, wherein a sensor bandwidth is controlled by an optical spring effect, and an effective temperature of the sensor is controlled by one of passive damping and feedback cold-damping.

10. An optical microelectromechanical system (OMEMS) device to detect acceleration, the OMEMS device comprising:
    an optomechanical accelerometer device comprising:
        a frame,
        a test mass,
        a plurality of nano-tethers coupling the test mass to the frame, and
        a zipper cavity structure formed by a portion of the test mass and an adjacent portion of the frame;
    an optical beam source configured to direct a light beam onto the zipper cavity structure; and
    an optical detector configured to detect a displacement of the test mass caused by an in-plane acceleration of the frame.

11. The OMEMS device of claim 10, wherein the optical detector is configured to detect the displacement of the test mass based on a variation of one of light transmission through and light reflection from the zipper cavity structure.

12. The OMEMS device of claim 10, wherein the zipper cavity structure includes two patterned photonic crystal nanobeams and a slot, one of the nanobeams formed as the portion of the test mass and another of the nanobeams formed as the portion of the frame, the nanobeams being separated by the slot.

13. The OMEMS device of claim 10, wherein the optomechanical accelerometer device is fabricated in a silicon nitride thin film.

14. The OMEMS device of claim 10, wherein the test mass includes one or more cuts to facilitate undercutting the optomechanical accelerometer device.

15. The OMEMS device of claim 10, further comprising one or more electrostatic actuators for in-situ tuning of an optical resonance of the zipper cavity structure and damping of a mechanical mode of the zipper cavity structure to enable closed-loop operation.

16. The OMEMS device of claim 10, further comprising a beam splitter configured to split the light beam, transmit a first portion of the split light beam through the zipper cavity structure, and transmit a second portion of the split light beam to the optical detector as a reference light beam.

17. The OMEMS device of claim 16, wherein the optical beam source is a laser source providing a laser beam and the optical detector is a balanced photo detector (BPD).

18. The OMEMS device of claim 17, further comprising a proportional-integral (PI) controller coupled to the optical detector, the PI controller configured to lock the laser beam half a line width red-detuned from an optical resonance of the zipper cavity structure.

19. A method to fabricate an optomechanical accelerometer device, the method comprising:
    forming a mask for accelerometer structures comprising a test mass, support nano-tethers, and a zipper cavity structure; and
    transferring the mask into a silicon nitride layer formed on a single-crystal silicon wafer.

20. The method of claim 19, further comprising forming the accelerometer structures in a single electron-beam lithography step.

21. The method of claim 19, further comprising growing the silicon nitride layer using low-pressure chemical vapor deposition (LPCVD) under conditions that enable large internal tensile stress in a range from approximately 0.5 to approximately 10 GPa.

22. The method of claim 19, wherein transferring the mask into the silicon nitride layer includes dry etching by inductively coupled plasma/reactive-ion etching (ICP/RIE).

23. The method of claim 19, further comprising undercutting the accelerometer structures employing anisotropic wet-etching.

24. The method of claim 19, further comprising preventing a collapse of the zipper cavity structure employing critical point drying in $CO_2$.

* * * * *

UNITED STATES PATENT AND TRADEMARK OFFICE
CERTIFICATE OF CORRECTION

PATENT NO.         : 9,618,531 B2
APPLICATION NO.    : 14/379744
DATED              : April 11, 2017
INVENTOR(S)        : Painter et al.

Page 1 of 1

It is certified that error appears in the above-identified patent and that said Letters Patent is hereby corrected as shown below:

In the Specification

In Column 1, Line 9, delete "§371." and insert -- § 371. --, therefor.

In Column 1, Line 13, above "BACKGROUND", insert
-- STATEMENT OF GOVERNMENT GRANT
This invention was made with government support under Grant No. W911NF-11-1-0173 awarded by the Army Research Office (ARO). The government has certain rights in the invention. --.

In Column 5, Line 45, delete "2.7 kHz" and insert -- 27 kHz --, therefor.

In Column 7, Line 30, delete "laser tight" and insert -- laser light --, therefor.

In Column 12, Line 37, delete "more out to" and insert -- more cuts to --, therefor.

In Column 15, Line 18, delete "being on associated" and insert -- being so associated --, therefor.

In Column 15, Line 56, delete "is explicit" and insert -- is explicitly --, therefor.

Signed and Sealed this
Twenty-fifth Day of July, 2017

Joseph Matal
*Performing the Functions and Duties of the
Under Secretary of Commerce for Intellectual Property and
Director of the United States Patent and Trademark Office*